United States Patent
Lyren

(10) Patent No.: US 9,308,093 B1
(45) Date of Patent: Apr. 12, 2016

(54) HIP IMPLANT WITH AN INTERFACE THAT CONNECTS A METAL NECK BODY TO A POROUS BONE FIXATION BODY

(71) Applicant: Four Mile Bay, LLC, Wadsworth, OH (US)

(72) Inventor: Philip Scott Lyren, Hong Kong (CN)

( * ) Notice: Subject to any disclaimer, the term of this patent is extended or adjusted under 35 U.S.C. 154(b) by 0 days.

(21) Appl. No.: 14/878,092

(22) Filed: Oct. 8, 2015

Related U.S. Application Data

(63) Continuation of application No. 13/947,069, filed on Jul. 21, 2013, now Pat. No. 9,265,612, which is a continuation of application No. 11/409,611, filed on Apr. 24, 2006, now Pat. No. 8,506,642, which is a continuation of application No. 10/446,069, filed on May 27, 2003, now abandoned.

(51) Int. Cl.
| | |
|---|---|
| *A61F 2/36* | (2006.01) |
| *A61F 2/30* | (2006.01) |
| *B22F 7/04* | (2006.01) |
| *A61F 2/28* | (2006.01) |

(52) U.S. Cl.
CPC ........... *A61F 2/3601* (2013.01); *A61F 2/30767* (2013.01); *B22F 7/04* (2013.01); *A61F 2002/2817* (2013.01); *A61F 2002/30013* (2013.01); *A61F 2002/3092* (2013.01); *A61F 2002/30125* (2013.01); *A61F 2002/30156* (2013.01); *A61F 2002/30158* (2013.01); *A61F 2002/30331* (2013.01); *A61F 2002/30354* (2013.01); *A61F 2002/30377* (2013.01); *A61F 2002/30403* (2013.01); *A61F 2002/30677* (2013.01); *A61F 2002/30968* (2013.01); *A61F 2002/3625* (2013.01); *A61F 2310/00023* (2013.01)

(58) Field of Classification Search
CPC ................ A61F 2002/3625; A61F 2002/3631; A61F 2/3662; A61F 2002/3678
See application file for complete search history.

(56) References Cited

U.S. PATENT DOCUMENTS 6,361,566 B1 * 3/2002 Al-Hafez .................. A61F 2/32 623/22.15

* cited by examiner

*Primary Examiner* — Yashita Sharma
*Assistant Examiner* — Daniel Bissing

(57) ABSTRACT

A hip implant having two distinct bodies, a neck body and a bone fixation body. The neck body is formed from a solid metal and has an interface for connecting to a femoral ball. The bone fixation body has an elongated shape and is formed as a porous structure that is inserted into an intramedullary canal of a patient.

15 Claims, 3 Drawing Sheets

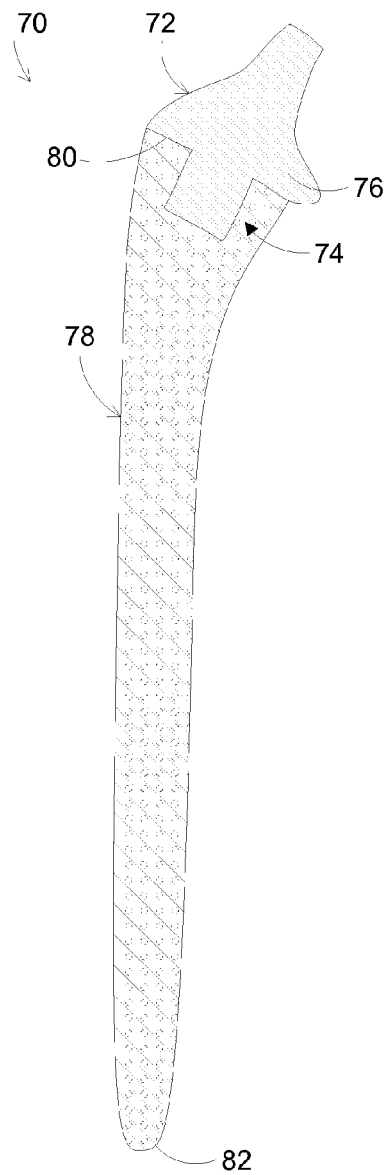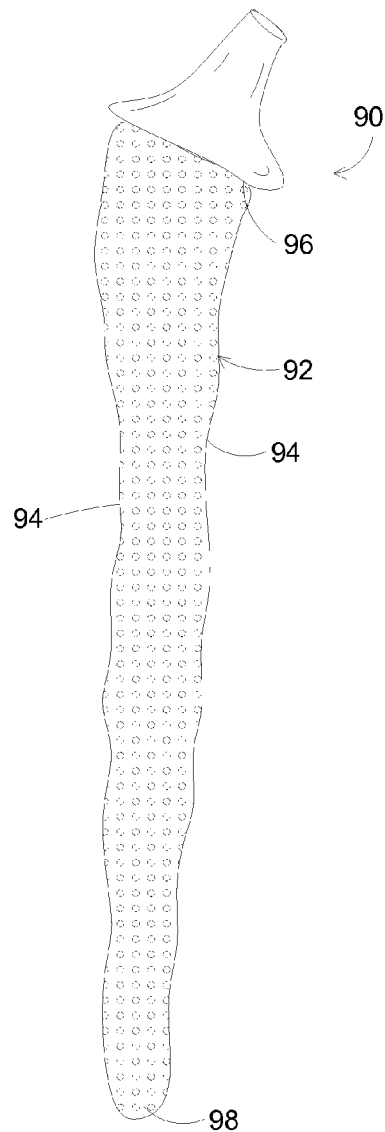
Fig. 5        Fig. 6
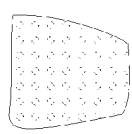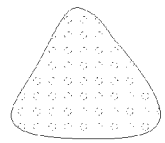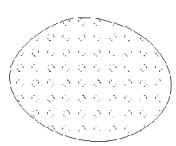
Fig. 7        Fig. 8        Fig. 9

HIP IMPLANT WITH AN INTERFACE THAT CONNECTS A METAL NECK BODY TO A POROUS BONE FIXATION BODY

FIELD OF THE INVENTION

The disclosure herein generally relates to hip implants for osseointegration into bone and, more particularly, to hip implants having a porous body.

BACKGROUND OF THE INVENTION

Much effort has been directed to integrating hip implants into surrounding bone. Ideally, a hip implant would be placed into the femur, and thereafter bone would readily grow into the surface of the implant. To achieve this objective, many different surface technologies have been applied to hip implants. In some instances, the surface of the implant is roughened, grit-blasted, plasma-sprayed, or microtextured. In other instances, the surface is coated with a biological agent, such as hydroxylapatite (known as HA). In all of these instances, the goal is the same: Produce a surface on the hip implant into which surrounding bone will grow or bond.

Porous coatings have also been applied to surfaces of hip implants. These coatings are advantageous since bone will indeed grow into a portion of the outer most surface of the implant. Osseointegration, to a limited extent then, has been achieved with porous coated surfaces. These surfaces though are far from ideal in terms of accepting and encouraging bone growth into the body of the implant.

As one disadvantage, porous surfaces are often thin coatings applied to the metallic substrate of the implant. Bone surrounding the implant can only grow into the thin coating itself. Bone cannot grow through the coating and into the metallic substrate. The depth of bone growth into the implant is limited to the depth of the porous coating. Bone simply cannot grow completely through the implant or deeply into the body of the implant.

It therefore would be desirable to have a hip implant that offers optimum anchoring in bone with bone growth into a porous body.

SUMMARY OF THE INVENTION

The present invention is directed toward a femoral hip implant for integrating with surrounding bone. In one exemplary embodiment, the implant includes two separate and distinct bodies, a neck body and a bone fixation body. Together, these bodies form a complete femoral hip implant.

The neck body is located at the proximal end of the implant and includes an interface adapted to connect with a femoral ball component. In an exemplary embodiment, this interface comprises an elongated cylindrical shaft or neck adapted to matingly engage with a cylindrical recess in the femoral ball component.

In one exemplary embodiment, the neck body is formed of a solid metal piece, such as titanium, titanium alloy, or other metals or alloys suitable for a hip prosthesis. The body is formed from a machining process and has a base portion that may comprise a collar. The neck extends outwardly away from the base portion.

The bone fixation body is formed of a porous metal, such as titanium or other metals or alloys suitable for a hip prosthesis. In one exemplary embodiment, the body is formed with a sintering process, is completely porous, and does not include a metal substrate. In cross section then, the body has a porous structure with no solid metal substrate.

The neck body (formed of solid metal) and the bone fixation body (formed of a completely porous structure) are permanently connected together. When connected, the two bodies form a hip implant. In one exemplary embodiment, these two bodies are connected with a sintering process.

In one exemplary embodiment, the bone fixation body portion of the hip implant is completely porous. This porous structure extends entirely through the body of the implant along the region where the implant engages femoral bone. As such, the depth of bone growth into the implant is not restricted to a thin porous coating. Instead, bone can grow deeply into the body of the implant or completely into and even through the body of the implant. The implant, then, can become fully integrated into surrounding bone with the structure of bone dispersed throughout the body of the implant.

In one exemplary embodiment, the geometric structure of the porous body may be shaped and sized to emulate the shape and size of natural bone surrounding the implant. Specifically, the porous structure of the bone fixation body thus replicates the porous structure of natural bone itself. The porous structure, thus, readily accepts and encourages surrounding bone to grow into and even through the body of the implant.

In one exemplary embodiment, the bone fixation body may be doped with bone growth agents to enhance and stimulate bone growth. These agents can be placed throughout the bone fixation body so bone grows deeply into the implant or completely through the implant. Bone growth, as such, is not restricted to the surface of the implant.

As noted, the porous structure of the implant enables bone to grow deeply into or completely through the implant itself. Growth deep into the body of the implant provides an extremely strong interface between the implant and surrounding natural bone. As such, the likelihood that the implant will loosen is greatly reduced. Further, the overall long-term acceptance of the implant in the bone is increased. Further yet, the porous structure of the bone fixation body reduces the overall weight of the hip implant.

BRIEF DESCRIPTION OF THE DRAWINGS

FIG. 5 is a side cross-sectional view of yet another exemplary embodiment of a hip implant of the present invention.

FIG. 6 is a side view of yet another exemplary embodiment of the present invention.

FIG. 7 is a top view of a horizontal cross section of an exemplary embodiment of the present invention.

FIG. 8 is a top view of a horizontal cross section of another exemplary embodiment of the present invention.

FIG. 9 is a top view of a horizontal cross section of yet another exemplary embodiment of the present invention.

DETAILED DESCRIPTION

Figure 1:
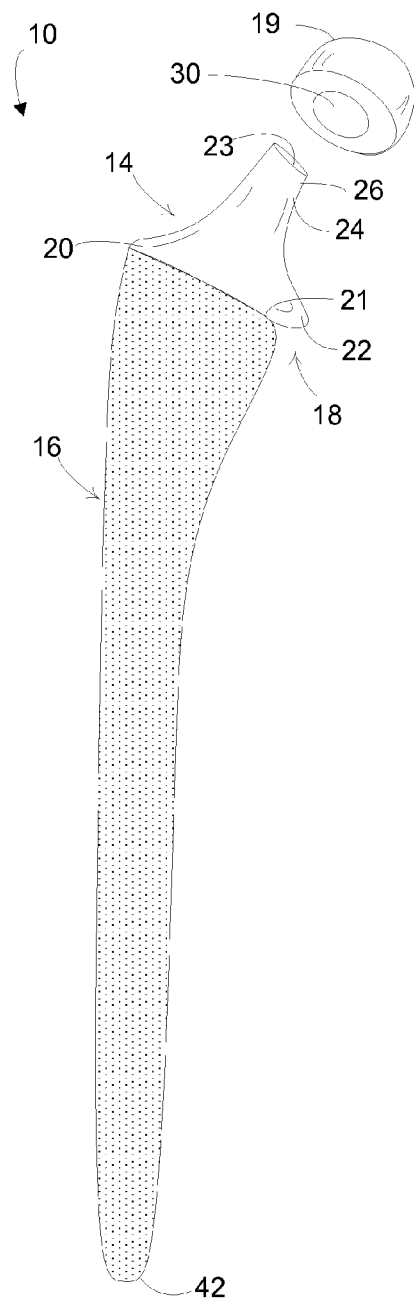
FIG. 1 is a side view of one embodiment of a hip implant of an exemplary embodiment of the present invention.
Figure 2:
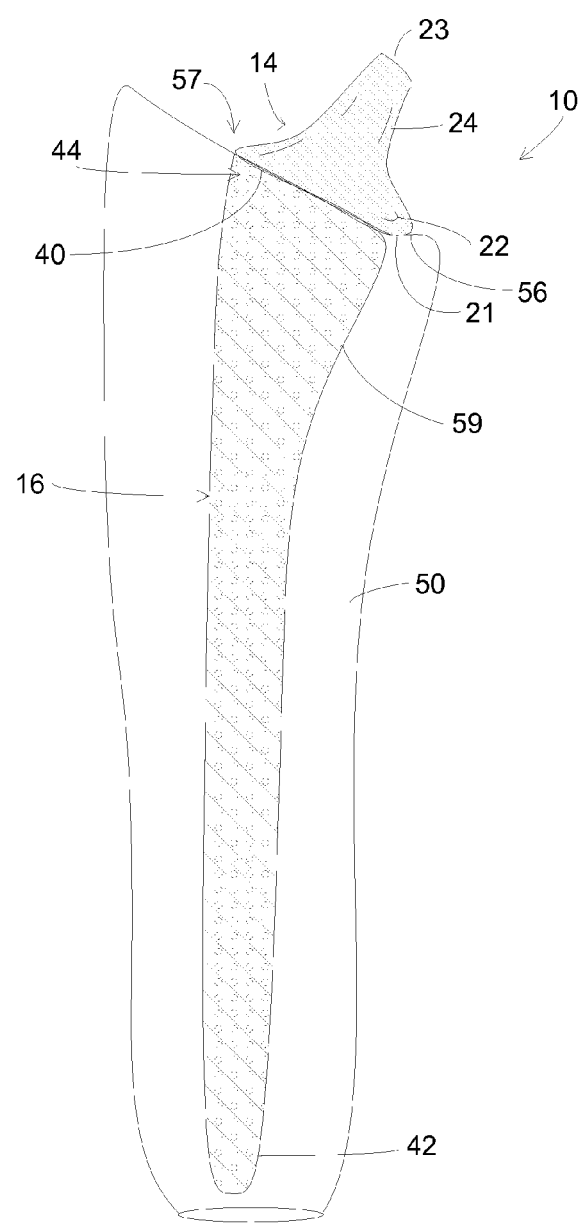
FIG. 2 is a cross-sectional view of the implant of FIG. 1 embedded in the intramedullary canal of a femur.

Referring to FIGS. 1 and 2, a hip implant 10 is shown according to an exemplary embodiment of the invention. Implant 10 is preferably constructed of a biocompatible material such as titanium, titanium alloy, or other metals or alloys suitable for a hip prosthesis. Implant 10 comprises two primary components or bodies, a neck body 14 and a bone fixation body 16.

The neck body 14 is located at the proximal end 18 of the hip implant 10 and functions to connect the hip implant 10 to a spherically shaped femoral ball 19 and acetabular component (not shown). The neck body extends from a flat or planar distal end surface 21 to a proximal end surface 23. Further, the neck body has a base portion 20 that includes a collar 22 adapted to seat against a resected or end portion of a femur. An interface is adapted to connect the neck body to the femoral ball. A neck portion 24 extends outwardly from the base portion 20. This neck portion has a short cylindrical configuration and has an end 26 with a slight taper. This end 26 is adapted to be received in a correspondingly shaped and sized cylindrical recess 30 in the femoral ball 19. Together, end 26 and recess 30 form a Morse taper connection.

Preferably, the neck body 14 is formed of a biocompatible metal, such as a solid metal piece of titanium, titanium alloy or other metals or alloys suitable for a hip prosthesis. The body can be machined to have a size and shape shown in the figures or other sizes and shapes adapted for use as a hip implant.

The bone fixation body 16 has an elongated tapering shape that extends from a flat or planar proximal end surface 40 to a rounded distal end surface 42. The distal end surface 21 of neck body 14 connects or fuses to the proximal end surface 40 of the bone fixation body 16 at a junction 44.

In the exemplary embodiments of FIGS. 1 and 2, bone fixation body 16 is formed from a porous metal, such as titanium. The body has a completely porous structure that extends throughout the entire body from the proximal end surface 40 to distal end surface 42. Specifically, as shown in FIG. 2, body 16 does not include a solid metal substrate.

FIG. 2 shows the implant 10 embedded in a femur 50 of a patient. In this embodiment, the implant is embedded into the intramedullary canal 52 of the femur. The length of the bone fixation body 16 extends along the region where the implant contacts surrounding bone. As shown, the collar 22 seats against a resected end 56 of the femur above an entrance 57 to the intramedullary canal 59. In this embodiment, the bone fixation body 16 extends into the intramedullary canal, and the neck body 14 extends outwardly from the resected end of the intramedullary canal and femur. Further, the proximal end surfaced 40 is adjacent the entrance 57 to the intramedullary canal.

As noted, the bone fixation body 16 has a porous structure that extends throughout the body from the proximal end surface to the distal end surface. By "porous," it is meant that the material at and under the surface is permeated with interconnected interstitial pores that communicate with the surface. The porous structure can be formed by sintering titanium, titanium alloy powder, metal beads, metal wire mesh, or other suitable materials, metals, or alloys known in the art.

The porous structure of body 16 is adapted for the ingrowth of cancellous and cortical bone spicules. In the exemplary embodiment, the size and shape of the porous structure emulates the size and shape of the porous structure of natural bone. Preferably, the average pore diameter of body 16 is about 40 μm to about 800 μm with a porosity from about 45% to 65%. Further, the interconnections between pores can have a diameter larger than 50-60 microns. In short, the geometric configuration of the porous structure should encourage natural bone to migrate and grow into and throughout the entire body 16.

Although specific ranges are given for pore diameters, porosity, and interconnection diameters, these ranges are exemplary and are applicable to one exemplary embodiment. In other embodiments, these ranges could be modified, and the resulting hip implant still within the scope of the invention.

Preferably, body 16 is created with a sintering process. One skilled in the art will appreciate that many variations exist for sintering, and some of these variations may be used to fabricate the present invention. In the exemplary embodiment, the neck body is formed from a solid piece of metal and prepared using conventional and known machining techniques. Next, a ceramic mold is provided. The mold has a first cavity that is sized and shaped to match the size and shape of the bone fixation body. In this first cavity, the sintering material can be placed. The mold also has a second cavity that is adjacent and connected to the first cavity. This second cavity is sized and shaped to receive the neck body. The neck body is positioned in the second cavity such that the distal end surface is adjacent and continuous with the first cavity.

The sintering material is then placed into the first cavity. This material may be a titanium alloy powder, such as Ti-6Al-4V. Some of this powder will contact the distal end surface of the neck body. The mold is then heated to perform the sintering process. During this process, as the material in the first cavity heats and sinters, the bone fixation body forms and simultaneously bonds or fuses to the distal end surface of the neck body.

The size and shape of the pores and porous structure produced in the first cavity depend on many factors, These factors include, for example, the temperature obtained in the furnace, the sintering time, the size and shape of sintering material, the composition of the sintering material, and the type of ceramic mold used. These factors (and others) can be varied to produce a bone fixation body in accordance with the present invention. Further, these factors (and others) can be varied to produce a strong bond between the bone fixation body and neck body.

Once the sintering process is finished, the neck body is directly fused to the bone fixation body. These two bodies are now permanently connected together to form the hip implant.

In the aforementioned sintering process, the bone fixation body simultaneously forms and attaches to the neck body. One skilled in the art though will appreciate that each of these bodies can be fabricated independently and subsequently connected together. If the bodies are made separately, then they may be attached or fused together using known welding or brazing techniques, for example.

In FIG. 1, for example, the bone fixation body has an elongated tapering body with a slight bow. The bone fixation body, though, may have other configurations and still be within the scope of the invention. The size and shape of the body depend on the size and shape of the cavity of the mold during the sintering process. This cavity can be shaped, for example, to emulate the natural size, shape, and contour of a human intramedullary canal. As such, the bone fixation body will more naturally fit into the intramedullary canal and conform to the natural anatomical contours of a human patient.

Figure 3:
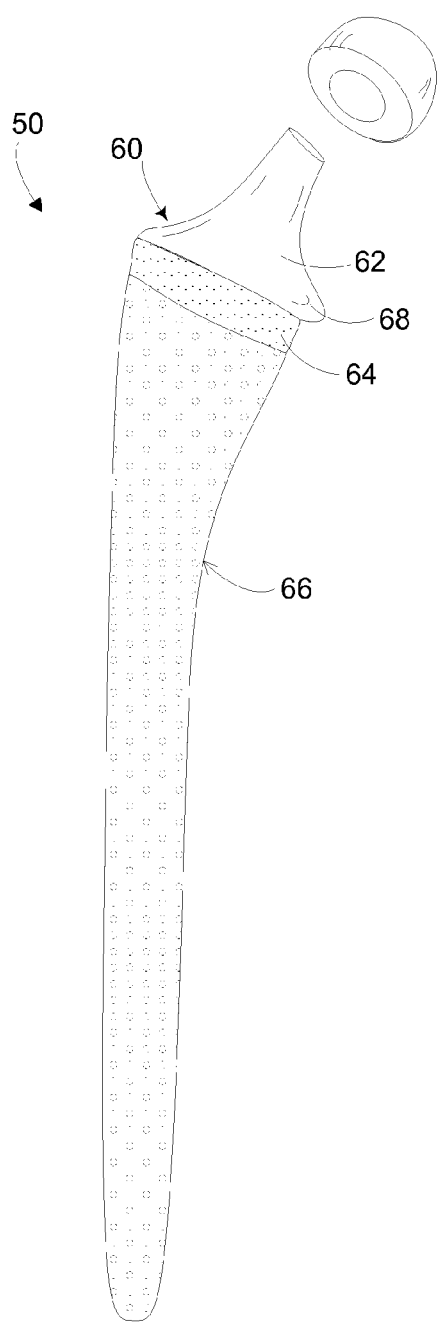
FIG. 3 is a side view of another exemplary embodiment of a hip implant of the present invention.
Figure 4:
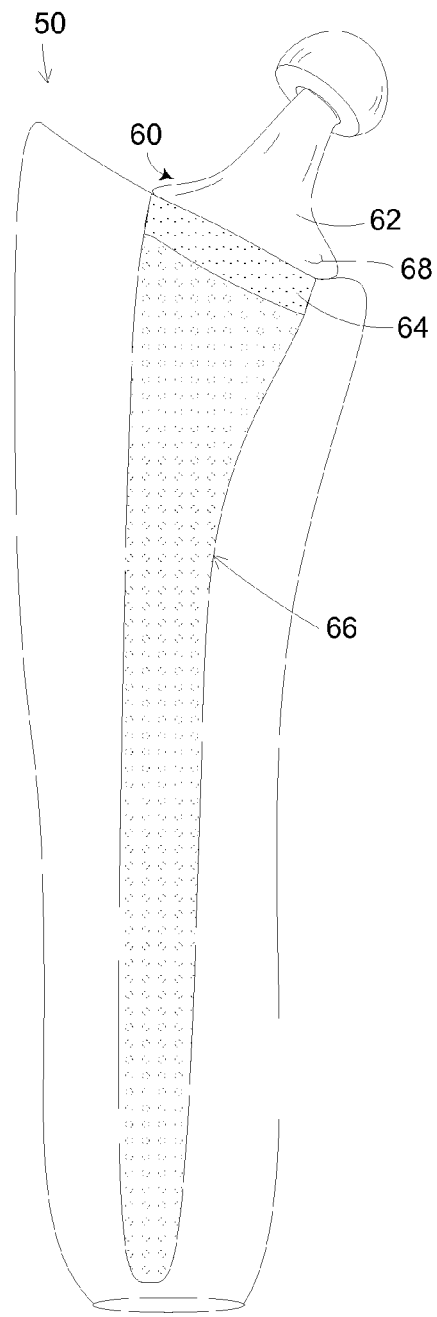
FIG. 4 is a cross-sectional view of FIG. 3 showing the hip implant embedded in the intramedullary canal of a femur.

FIGS. 3 and 4 show another hip implant 50 according to an exemplary embodiment of the invention. With some differences, implant 50 is similarly configured to the implant 10. As one difference, the neck body 60 of implant 50 has two different and distinct regions on its outer surface. A first region 62 has a smooth outer surface. A second region 64 has a bone-engaging surface that is contiguous and adjacent to the first region 62 on one side and contiguous and adjacent the porous bone fixation body 66 on the other side. The second region is non-porous and is shaped as a band that extends completely around the neck body. This second region can be formed on the outer surface of the neck body with various techniques. These techniques include, for example, coating with HA, grit-blasting, etching, micro-texturing, other non-porous surface treatments, or combinations of these techniques. This surface 64 is provided as an intermediate zone between the porous body and the smooth first region 62.

As shown in FIG. 4, the second region 64 is below collar 68 and is positioned into the intramedullary canal to contact bone. Region 64, then, contacts bone, and region 62 does not contact bone and extends above it.

FIG. 5 shows another implant 70 according to another exemplary embodiment of the invention. With some differences, implant 70 is similarly configured to the implant 10. As one difference, neck body 72 includes a male protrusion 74 that extends outward from base portion 76. This protrusion 74 is adapted to extend partially into the bone fixation body 78 of implant 70.

The protrusion 74 forms a core for the bone fixation body. As shown in FIG. 5, this protrusion extends past the proximal end surface 80 and into the bone fixation body. The depth of the protrusion into the bone fixation body can be increased or decreased in various embodiments and still remain within the scope of the invention. For example, the protrusion can partially extend into the bone fixation body and remain substantially near the proximal end surface. Alternatively, the protrusion can extend farther into the bone fixation body toward the distal end surface 82. In this latter embodiment, the protrusion gradually tapers as it extends toward the distal end surface.

The size and shape of the protrusion can also have various embodiments and still remain within the scope of the invention. For example, the protrusion can be cylindrical or polygonal, such as rectangular or square. Other configurations are possible as well; the protrusion can taper or have longitudinal ribs placed along its outer surface. The size and shape of the protrusion can have various embodiments to serve various functions. For example, the protrusion can be sized and shaped to provide a strong connection between the neck body and bone fixation body. The protrusion can be sized and shaped to provide an anti-rotational interface between the neck body and bone fixation body. Further, the protrusion can be sized and shaped to provide additional strength to the bone fixation body or more equally or efficiently distribute loads from the neck body to the bone fixation body. Other factors as well may contribute to the design of the protrusion.

FIG. 6 shows another implant 90 according to an exemplary embodiment of the invention. Implant 90 has a bone fixation body 92 with an outer surface that has a plurality of undulations 94, such as hills and valleys. These undulations may be provided as tiny ripples or waves. Alternatively, the undulations may be larger and more rolling. Regardless, the undulations are adapted to firmly secure the implant into the intramedullary canal of the femur after the implant is placed therein.

As shown in FIG. 6, the undulations extend along the entire length of the bone fixation body 92 from the proximal end surface 96 to the distal end surface 98. In alternative embodiments, the undulations do not extend along the entire length of the bone fixation body, but partially extend along this body.

FIGS. 7-9 show various longitudinal cross-sectional shapes of the bone fixation body for different exemplary embodiments of the invention. The bone fixation body may have one single longitudinal cross-sectional shape, or the body may have numerous different longitudinal cross-sectional shapes. FIGS. 7-9 represent examples of some of these shapes.

FIG. 7 shows a trapezoidal longitudinal cross-sectional shape. FIG. 8 shows a triangular longitudinal cross-sectional shape. FIG. 9 shows an elliptical or oval longitudinal cross-sectional shape.

The bone fixation body can be adapted to induce bone growth partially into or entirely through the body. The body, for example, can be doped with biologically active substances. These substances may contain pharmaceutical agents to stimulate bone growth all at once or in a timed-release manner. Such biological active substances are known in the art.

Although illustrative embodiments have been shown and described, a wide range of modifications, changes, and substitutions is contemplated in the foregoing disclosure; and some features of the embodiments may be employed without a corresponding use of other features. Accordingly, it is appropriate that the appended claims be construed broadly and in a manner consistent with the scope of the embodiments disclosed herein.

What is claimed is:

1. A method, comprising:
   machining a neck body from solid metal to have a base portion, a neck portion that extends outwardly from the base portion and includes a cylindrical configuration with a taper that receives a femoral ball, and a male protrusion that extends outwardly from the base portion oppositely from the neck portion and has an elongated shape that tapers and has a polygonal shape in a cross-sectional view;
   fabricating, separately from the neck body, a bone fixation body that is formed of a porous metal structure without a solid metal substrate but with the porous metal structure that extends throughout the bone fixation body, has a size and a shape that emulate a size and a shape of a porous structure of natural human bone, has a trapezoidal shape in a cross-sectional view, and has a tapering body with an external bow; and
   permanently connecting, after the bone fixation body is separately fabricated from the neck body, the bone fixation body to the neck body at an interface where the male protrusion extends into and engages the bone fixation body and forms a core for the bone fixation body, the bone fixation body abuts the base portion of the neck body, and the bone fixation body abuts the polygonal shape of the male protrusion in order to provide anti-rotation at the interface between the neck body and the bone fixation body.

2. The method of claim 1, wherein the bone fixation body has a size and a shape to distribute loads from the neck body to the bone fixation body.

3. The method of claim 1, wherein the bone fixation body has a size and a shape that emulate a size and a shape of a human intramedullary canal.

4. The method of claim 1, wherein the bone fixation body is fused to the male protrusion of the neck body after the bone fixation body is formed.

5. The method of claim 1, wherein the bone fixation body is bonded to the male protrusion of the neck body after the bone fixation body is formed.

6. The method of claim 1, wherein the male protrusion also includes a circular shape in a cross-sectional view.

7. A method, comprising:
   machining, from solid metal, a neck body that includes a base portion, a neck portion that extends outwardly from the base portion and has a cylindrical configuration with a taper that receives a femoral ball, and a male protrusion that extends outwardly from the base portion oppositely from the neck portion and has an elongated shape that tapers and has a non-circle shape in a cross-sectional view;

making, separately from the neck body, a bone fixation body that is formed of a completely porous metal structure without a solid metal substrate, has a size and a shape that emulate a size and a shape of a porous structure of natural human bone, has a trapezoidal shape in a cross-sectional view, and has a tapering body with an external bow; and permanently attaching, after the bone fixation body is separately made from the neck body, the bone fixation body to the neck body at an interface that occurs where the male protrusion extends into and engages the bone fixation body to form a core for the bone fixation body, where the bone fixation body engages the base portion of the neck body, and where the bone fixation body engages the non-circle shape of the male protrusion and provides anti-rotation at the interface where the neck body and the bone fixation body attach.

8. The method of claim 7, wherein the bone fixation body has a size and a shape to distribute loads from the neck body to the bone fixation body.

9. The method of claim 7, wherein the bone fixation body has a size and a shape that emulate a size and a shape of a human intramedullary canal.

10. The method of claim 7, wherein the bone fixation body is fused to the male protrusion of the neck body after the bone fixation body is formed.

11. The method of claim 7, wherein the bone fixation body is bonded to the male protrusion of the neck body after the bone fixation body is formed.

12. The method of claim 7, wherein the male protrusion also includes a circular shape in a cross-sectional view.

13. A method, comprising:
machining a neck body from solid metal to have a base portion, a neck portion that extends outwardly from the base portion and includes a cylindrical configuration with a taper that receives a femoral ball, and a male protrusion that extends outwardly from the base portion oppositely from the neck portion and has an elongated shape that tapers and has a polygonal shape in a cross-sectional view;

fabricating, separately from the neck body, a bone fixation body that has a tapering cylindrical body with an external bow on one side and with a trapezoidal shape in a cross-sectional view and that is formed of a porous metal structure without a solid metal substrate such that the porous metal structure extends throughout the bone fixation body, has a porosity with values that include 45% to 65%, and has a size and a shape that emulate a size and a shape of a porous structure of natural human bone; and permanently connecting, after the bone fixation body is separately fabricated from the neck body to have the tapering cylindrical body with the external bow on one side and with the trapezoidal shape, the bone fixation body to the neck body to form a hip implant such that the male protrusion forms a core for the bone fixation body, the bone fixation body abuts the base portion of the neck body, and the bone fixation body abuts the polygonal shape of the male protrusion in order to provide anti-rotation between the neck body and the bone fixation body.

14. The method of claim 1, wherein the porous metal structure is fabricated to have a porosity with values that include 45% to 65%.

15. The method of claim 7, wherein the porous metal structure is made to have a porosity with values that include 45% to 65%.

* * * * *